(12) United States Patent
Simons et al.

(10) Patent No.: US 6,448,395 B1
(45) Date of Patent: *Sep. 10, 2002

(54) PROCESS FOR PURIFYING CAPROLACTAM

(75) Inventors: Antonius J. F. Simons, Geleen; Louise A Groot Zevert, Sittard, both of (NL)

(73) Assignee: DSM N.V., Heerlen (NL)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/398,435

(22) Filed: Sep. 17, 1999

Related U.S. Application Data

(63) Continuation of application No. PCT/NL98/00152, filed on Mar. 16, 1998.

(30) Foreign Application Priority Data

Mar. 17, 1997 (BE) .............................................. 9700230

(51) Int. Cl.$^7$ ........................................... C07D 201/16
(52) U.S. Cl. ...................................................... 540/540
(58) Field of Search .......................................... 540/540

(56) References Cited

U.S. PATENT DOCUMENTS

| 3,485,820 A | * 12/1969 | Hoffmann et al. ....... 260/239.3 |
| 3,485,821 A | 12/1969 | Wicks ........................... 150/1 |
| 3,761,467 A | 9/1973 | Williams et al. ...... 260/239.3 A |
| 3,850,910 A | * 11/1974 | Goettsch et al. ......... 260/239.3 |
| 4,036,830 A | * 7/1977 | De Rooij et al. ........ 260/239.3 |
| 4,170,592 A | * 10/1979 | Danziger et al. ..... 260/239.3 A |

FOREIGN PATENT DOCUMENTS

| DE | 3820737 | 12/1989 |
| EP | 0 002 300 | 6/1979 |
| GB | 1 251 258 | 10/1971 |
| GB | 1 430 006 | 3/1976 |
| GB | 1 534 775 | 12/1978 |
| GB | 1 556 943 | 12/1979 |
| WO | 9730028 | 8/1997 |

* cited by examiner

*Primary Examiner*—Bruck Kifle
(74) *Attorney, Agent, or Firm*—Pillsbury Winthrop LLP

(57) ABSTRACT

Process for purifying an aqueous caprolactam mixture by extracting the caprolactam with the aid of an organic caprolactam solvent that is not miscible with water in a benzene extraction, and releasing the caprolactam from the organic solvent by means of extraction with water, with the formation of an aqueous caprolactam solution, in a back extraction, with at least a separate pre-extraction taking place before the benzene extraction and/or the back extraction, in which, in a pre-extraction before the benzene extraction, an organic solvent that is not miscible with water is used for the extraction and, in a pre-extraction before back extraction, water is used for the extraction.

27 Claims, 2 Drawing Sheets

PROCESS FOR PURIFYING CAPROLACTAM

CROSS-REFERNCE TO RELATED APPLICATIONS

This application is a continuation of Application PCT/NL98/00152, filed Mar. 16, 1998, which in turn, claims priority from BE 9700230 filed Mar. 17, 1997.

The invention relates to a process for purifying an aqueous caprolactam mixture by extracting the caprolactam with the aid of an organic caprolactam solvent that is not miscible with water in a benzene extraction, and releasing the caprolactam from the organic solvent by means of extraction with water, with the formation of an aqueous caprolactam solution, in a back extraction.

Such a process is known from NL-A-77110150, which describes the so-called benzene extraction of caprolactam from water to benzene and the back extraction from benzene to water. The drawback of this process, however, is that if the columns are more heavily loaded, for example if the caprolactam production is increased, this will adversely affect the extraction yield of the extraction columns employed.

The aim of the invention is now to provide a process in which the extraction steps can be more heavily loaded without loss of extraction yield.

This aim is achieved because at least a separate pre-extraction takes place before the benzene extraction and/or the back extraction, in which, in a pre-extraction before the benzene extraction, an organic solvent that is not miscible with water is used for the extraction and, in a pre-extraction before back extraction, water is used for the extraction.

This makes it possible to increase the load of any extraction step by 20% with only one extra theoretical tray; it moreover even leads to an improved extraction yield. Purifying caprolactam by means of benzene extraction and back extraction often implies a bottleneck in the production of caprolactam, because the extraction columns are unable to process the increasing caprolactam productions. This problem can now be simply solved even without having to install extra equipment, for example columns, by causing a pre-extraction to take place. New extraction columns are moreover expensive and it is often difficult to incorporate them in an existing installation.

This pre-extraction can take place in for example a mixer/settler. A mixer/settler is an apparatus comprising a mixing part and a settling part. The liquids are combined in the mixing part and energy is supplied to them, for example by means of a stirrer. This results in the formation of droplets of one of the liquids in the other, a dispersion. The dispersion then remains in the settling part for a sufficient length of time for the droplets to coalesce, preferably with a laminar flow.

Suitable mixer/settlers are the box-type mixer/settlers, the IMI, the "General Mills" or the Kemira mixer/settlers, described in "Liquid-Liquid Extraction Equipment" by Godfrey J. C. and Slater M. J., Ed. Wiley, COP (1994), Ch.I, pp. 294–297.

It is also possible to place an extension on a column, which extension may optionally also be widened.

Caprolactam-containing mixtures can for example be extracted with the aid of extraction columns. Columns fitted with rotating internally installed elements, known as 'rotating disc columns' (RDCs), and elements for pulsing the liquid column are suitable for use as extraction columns. Pulsing columns with packing bodies, pulsing columns with sieve trays, asymmetrical rotating disc contactors (ARD), Scheibel columns and Kühni columns are also suitable. In general it will suffice to carry out the process in a column comprising 3–25 theoretical trays, depending on the desired degree of purification. It is of course possible to increase the number of trays if so desired. The extraction process is preferably carried out in countercurrent mode, because the extraction will then proceed in the most efficient, and hence an economic, manner.

In one embodiment of the invention the caprolactam-containing mixture is, in the benzene extraction, first introduced into for example the mixer/settler as a pre-extraction step, to which the organic solvent obtained from an extraction step, for example a column, is added. Next, the two phases are intensively mixed for some time. With respect to the mixing time it is important that physical equilibrium is almost achieved. The mixing time will usually be between 5 minutes and half an hour. Then the mixture is introduced into the settling part, where the dispersion obtained can settle, which results in a separate water phase, which is subsequently separated, and a separate organic phase. Next, the separated water phase is fed to the top side of the benzene extraction column. It is also possible to feed a portion of the dispersion from the mixer/settler to the top of the extraction column and another portion to the column at a point for example at one third of the extraction column's height. The extraction medium is fed to the bottom of the extraction column.

It is not necessary to feed the (total) amount of the extraction media to the top (or bottom) of the column or the mixer/settler. A portion, or the entire amount, of the extraction media can optionally be fed into the top (or bottom) third part of the extraction column and/or to the side of the mixer/settler.

It is possible to carry out several benzene extractions and/or back extractions.

The pre-extraction can be carried out before the benzene extraction or before the back extraction or before both extraction steps. The pre-extraction preferably takes place on the concentrated side(s) of a benzene extraction and/or back extraction.

The pre-extraction preferably takes place in a mixer/settler. It is of course also possible to use several mixer/settlers.

The temperature at which the pre-extraction step before the first step takes place lies between 20 and 80° C. The temperature of the pre-extraction step before a second extraction lies between 10 and 60° C.

In the benzene extraction step also other extraction media can be used. Suitable extraction media for the benzene extraction are benzene, toluene, xylene, chloroform, chlorinated hydrocarbons or higher alcohols, i.e. mono- or polyhydric alcohols with 5–12 C. atoms. These extraction media may also contain caprolactam.

In the case of the back extraction the extraction medium is usually water or a solution of caprolactam in water.

The extraction media are preferably recycled and reused. Optionally this reuse of the extraction media can occur after purification of the used media.

Figure 1:
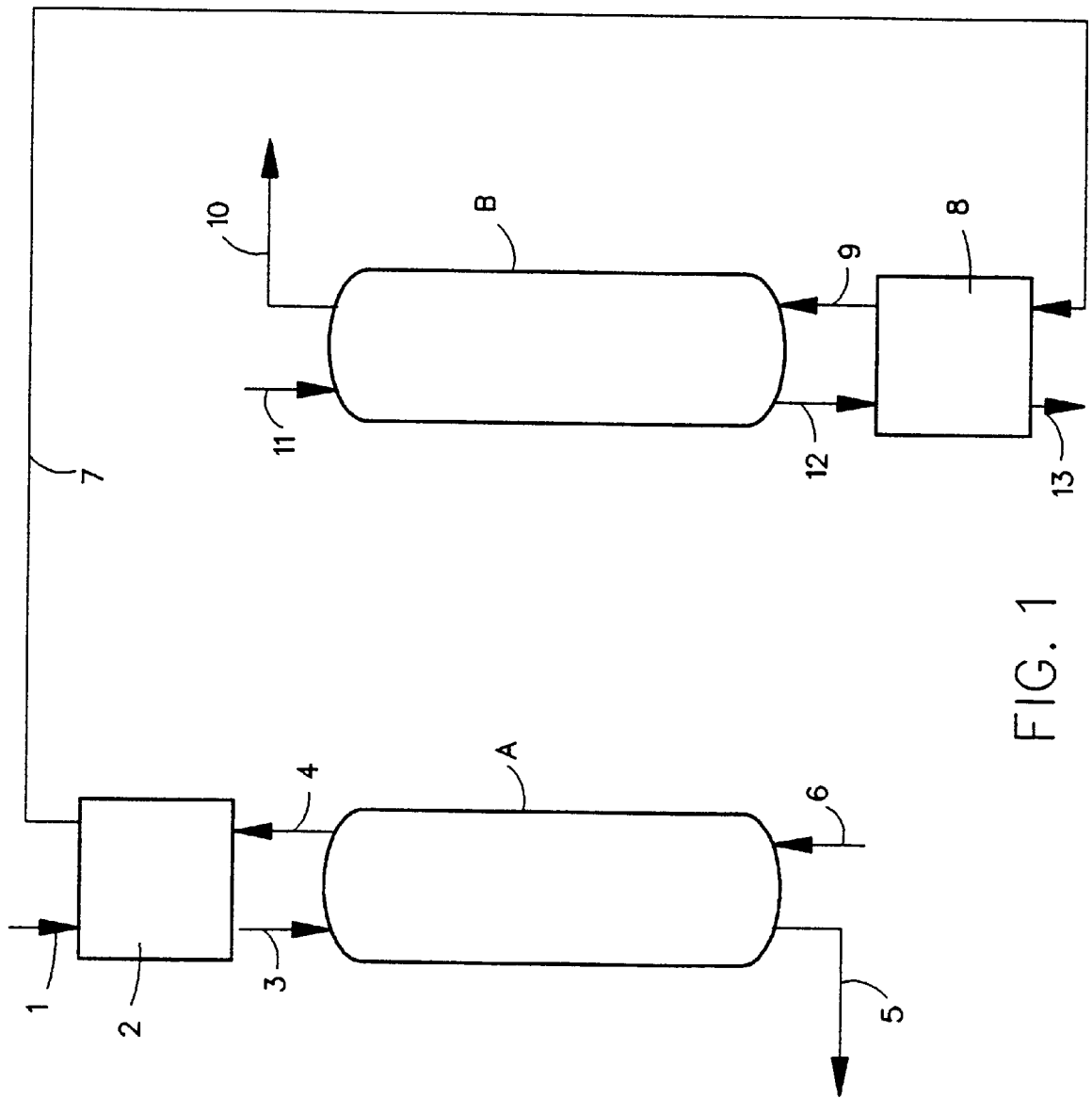
FIG. 1 is a schematic flow diagram of an embodiment of the invention process using two extraction columns and two pre-extraction mixer-settlers.

An embodiment of the process according to the invention is schematically illustrated in FIG. 1, in which A and B represent extraction columns. A caprolactam/water mixture is fed to a mixer/settler 2 via pipe 1. In addition, an organic solvent, for example benzene or benzenic lactam, is fed to the mixer/settler 2, via pipe 4. The pre-extracted aqueous caprolactam-containing feed is fed to column A via pipe 3. organic solvent is fed into column A in countercurrent mode via pipe 6 to extract the caprolactam from the aqueous solution. An aqueous solution from which the greater part of the caprolactam has been released is discharged via pipe 5. The organic caprolactam solution is returned to mixer/settler 2 via pipe 4, after which it is fed to mixer/settler 8 via pipe 7. Via pipe 9 the organic caprolactam solution is fed to extraction column B, in which back extraction of caprolactam takes place with the aid of water supplied via pipe 11. Solvent from which almost all the caprolactam has been removed is discharged via pipe 10, to be reused as an extraction medium for the caprolactam/water mixture.

The solution of caprolactam in water obtained from column B is fed to mixer/settler 8 via pipe 12, and conveyed on from there via pipe 13 for further processing.

The invention will be further demonstrated with reference to the following non-limiting examples.

COMPARATIVE EXPERIMENT A

Figure 2:
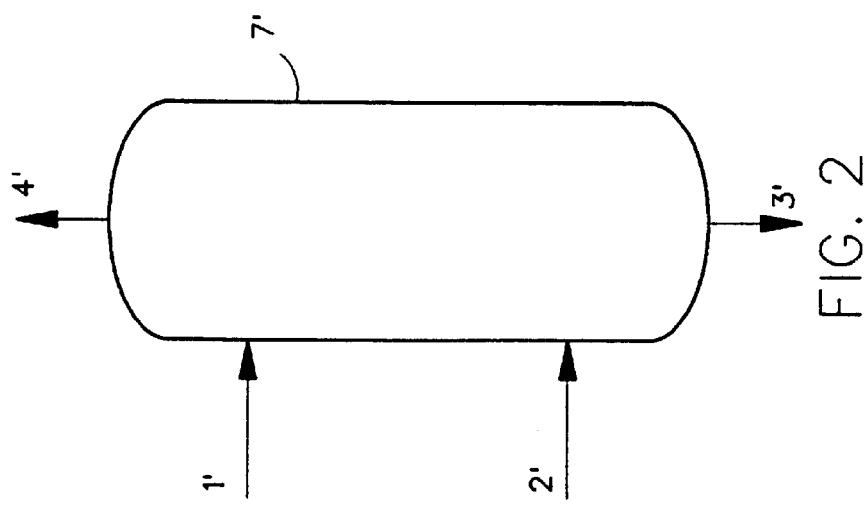
FIG. 2 is a schematic flow diagram of an arrangement according to the prior art.

An aqueous caprolactam mixture containing 71.9 wt.% caprolactam was extracted with the aid of benzene in a so-called 'rotating disc column' (RDC) with a length of 4.5 m and a diameter of 7.5 cm; see FIG. 2. The discs rotated at a speed of 400 rotations per minute (rpm). The aqueous caprolactam was fed to the top of the column (7') via feed (1') at a flow rate of 30 l/h. Benzene was fed to the bottom via stream (2') at a flow rate of 84 l/h. The extraction yield was optimized by varying the amount of rotating energy supplied. The outgoing water phase (3') contained 0.4 wt. % caprolactam, the outgoing benzene phase (4') 22 wt. % caprolactam. The extraction yield is based on the amount of caprolactam in (3'), relative to the amount of caprolactam in the feed (1'), is 99.5%

EXAMPLE I

Figure 3:
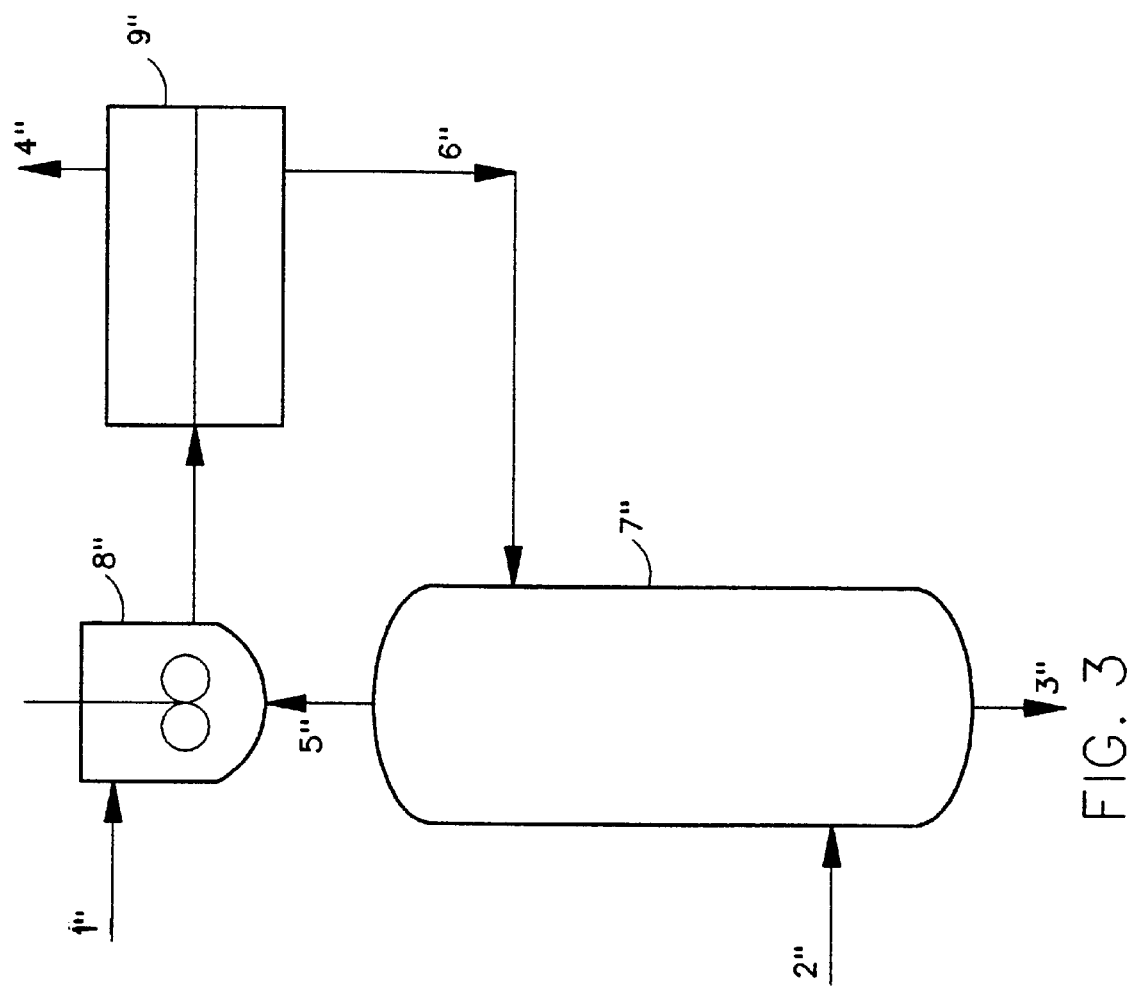
FIG. 3 is a schematic flow diagram of another embodiment of the invention process using a single extraction column with a pre-extraction mixer-settler.

Comparative Experiment A was repeated, only now a mixer/settler combination was placed before the column; see FIG. 3. The mixer (8") was a stirred vessel with a height of 15 cm and a diameter of 30 cm. The residence time in the mixer was 5 minutes. The settler (9") was a rectangular container measuring 0.6 by 0.3 by 0.2 m. The residence time in the settler was 10 minutes. The rotation speed in the rdc was 700 rpm. The flow rates of the aqueous caprolactam mixture and the benzene were increased by 25%. The flow rate of feed (1") was 37.5 l/h, and that of stream (2") 105 l/h. The outgoing water phase (3") contained only 0.2 wt. % caprolactam, while the outgoing benzene phase (4") still contained 22 wt. % caprolactam. The extraction yield was 99.8%, while the capacity of the extraction-steps combination had moreover been increased by 25%.

COMPARATIVE EXPERIMENT B

An aqueous caprolactam mixture containing 71% caprolactam was extracted with the aid of toluene in a 'pulsed packed column' (ppc) with a length of 5 m and a diameter of 5 cm. The aqueous caprolactam mixture was fed to the top of the column (7') via feed (1') at a flow rate of 7.6 kg/h; see FIG. 2. Toluene was fed to the bottom via stream (2') at a flow rate of 28 kg/h. The pulsation speed in the column varied from 0.005 to 0.02 m/s. The outgoing water phase (3') contained 8 wt. % caprolactam, the outgoing toluene phase (4') 17 wt. % caprolactam. The extraction yield was based on the amount of caprolactam in (3') relative to the amount of caprolactam in the feed (1') and was 93%.

EXAMPLE II

Comparative Experiment B was repeated, only now a mixer/settler combination as described in Example I was placed before the column; see FIG. 3. The residence time in the mixer was 6 minutes. The residence time in the settler was 10 minutes. The flow rates of feed (1") and stream (2") were increased by 20%. The flow rate of feed (1") was 9.1 kg/h and that of stream (2") 34 kg/h. The outgoing water phase (3") contained only 5 wt. % caprolactam, while the outgoing toluene phase (4") still contained 17 wt. % caprolactam. The extraction yield was 96%, while the capacity of the extraction steps had moreover been increased by 20%.

COMPARATIVE EXPERIMENT C

An aqueous caprolactam mixture containing 71 wt. % caprolactam was extracted with the aid of benzene in a ppc with a height of 6 m and a diameter of 0.23 m. The aqueous caprolactam mixture was fed to the top of the column (7') via feed (1') at a flow rate of 123 kg/h; see FIG. 2. Benzene was fed to the bottom via stream (2') at a flow rate of 243 kg/h. The pulsation rate in the column varied between 0.006 and 0.0125 m/s.

The outgoing water phase (3') contained approx. 1.5 wt. % caprolactam, the outgoing benzene phase (4') approximately 20 wt. % caprolactam. The extraction yield was based on the amount of caprolactam in (3') relative to the amount of caprolactam in the is feed (1') and was 99.4%.

EXAMPLE III

Comparative Experiment C was repeated, only now a mixer/settler combination as described in Example I was placed before the column; see FIG. 3. The residence time in the mixer was 5 minutes. The residence time in the settler was 11 minutes. The flow rates of feed (1") and stream (2") were increased by 25%. The extraction yield was 99.8%.

COMPARATIVE EXPERIMENT D

A benzenic caprolactam mixture containing 20 wt. % caprolactam was subjected to back extraction using water in a ppc with a height of 8 m and a diameter of 0.10 m. The water was fed to the top of the column (7') at a flow rate of 50 kg/h; see FIG. 2. The benzenic caprolactam mixture (2') was fed to the bottom at a flow rate of 103 kg/h. The pulsation rate in de column was 0.02 m/s. The outgoing water phase (3') contained approx. 28 wt. % caprolactam, the outgoing benzene phase (4') approx. 0.05 wt. % caprolactam. The extraction yield was 99.0%.

EXAMPLE IV

Comparative Experiment D was repeated, only now a mixer/settler combination as described in Example I was placed at the bottom of the column. Residence time in the mixer was 7 minutes. Residence time in the settler was 10 minutes. While the pulsation rate remained unchanged the flow rates of streams (1") and (2") were increased to 60 kg/h (1") and 124 kg/h (2"). The outgoing benzene phase contained only 0.02 wt. % caprolactam. The extraction yield was 99.9%.

What is claimed is:

1. A process for purifying an aqueous caprolactam mixture comprising:
   a) countercurrently extracting the caprolactam in an extraction column with the aid of an organic solvent for caprolactam that is not miscible with water to form an organic solvent-caprolactam mixture, and
   b) releasing the caprolactam from the organic solvent-caprolactam mixture by means of extraction with water,
   c) (i) pre-extracting said aqueous caprolactam mixture in a mixer/settler with an organic solvent before step a) and/or (ii) pre-extracting said organic solvent-caprolactam mixture in a mixer/settler with water before step b).

2. The process according to claim 1, wherein the pre-extraction takes place on the concentrated side(s) of step a) and/or step b).

3. The process according to claim 1, wherein the pre-extraction before step a) takes place at a temperature of between 20° C. and 80° C.

4. The process according to claim 1, wherein the pre-extraction before step b) takes place at a temperature between 10° C. and 60° C.

5. The process as claimed in claim 1, wherein the pre-extraction in a mixer/settler takes place before said step a).

6. The process as claimed in claim 1, wherein the pre-extraction in a mixer/settler takes place before said step b).

7. A process for extracting caprolactam from an aqueous caprolactam mixture comprising extracting the caprolactam with the aid of an organic solvent for caprolactam which is not miscible with water in a countercurrent extraction column, wherein a pre-extraction with an organic solvent immiscible with water in a mixer/settler is conducted prior to said extraction in the extraction column.

8. The process as claimed in claim 7, wherein said pre-extraction takes place on the concentrated side of the extraction.

9. The process according to claim 7, wherein said pre-extraction step takes place at a temperature of between 20° C. and 80° C.

10. The process according to claim 8, wherein said pre-extraction step takes place at a temperature of between 20° C. and 80° C.

11. The process as claimed in claim 1, wherein said organic caprolactam solvent that is not miscible with water is benzene.

12. The process as claimed in claim 7, wherein said organic caprolactam solvent that is not miscible with water is benzene.

13. The process as claimed in claim 1, wherein said organic solvent for caprolactam that is not miscible with water is selected from the group consisting of benzene, toluene, xylene, chloroform, chlorinated hydrocarbons, and mono- or polyhydric $C_5$–$C_{12}$ alcohols.

14. The process as claimed in claim 7, wherein said organic caprolactam solvent that is not miscible with water is selected from the group consisting of benzene, toluene, xylene, chloroform, chlorinated hydrocarbons, and mono- or polyhydric $C_5$–$C_{12}$ alcohols.

15. The process as claimed in claim 1, wherein the extraction column comprises at least 3 theoretical trays.

16. The process as claimed in claim 1, wherein the extraction column comprises 3–25 theoretical trays.

17. The process as claimed in claim 7, wherein the extraction column comprises at least 3 theoretical trays.

18. The process as claimed in claim 7, wherein the extraction column comprises 3–25 theoretical trays.

19. The process as claimed in claim 1, wherein the extraction of step (b) takes place in a countercurrent extraction column.

20. A process for increasing the load of a system for purifying an aqueous caprolactam mixture comprising:
   a) countercurrently extracting the caprolactam in an extraction column with the aid of an organic solvent for caprolactam that is not miscible with water to form an organic solvent-caprolactam mixture, and
   b) releasing the caprolactam from the organic solvent-caprolactam mixture by means of extraction with water,
   c) (i) pre-extracting said aqueous caprolactam mixture in a mixer/settler with an organic solvent before step a) at a flow rate of the aqueous caprolactam mixture to the system comprising the countercurrent extraction column and the mixer/settler which is increased, relative to the flow rate in the absence of said mixer/settler, without loss of extraction yield and/or (ii) pre-extracting said organic solvent-caprolactam mixture in a mixer/settler with water before step b) wherein the flow rate of the organic solvent-caprolactam mixture to the systemcomprising the countercurrent extraction column and the mixer/settler may be increased, relative to the flow rate in the absence of said mixer/settler, without loss of extraction yield.

21. A process for extracting caprolactam from an aqueous caprolactam mixture comprising extracting the caprolactam with the aid of an organic solvent for caprolactam which is not miscible with water in a system comprising a countercurrent extraction column and a mixer/settler, wherein a pre-extraction with an organic solvent immiscible with water in the said mixer/settler is conducted prior to said extraction with said organic solvent in the extraction column, and wherein the flow rate of the aqueous caprolactam mixture to the system is increased, relative to the flow rate in the absence of said mixer/settler, without loss of extraction yield.

22. Process according to claim 20, wherein said flow rate is increased by at least 20%.

23. Process according to claim 21, wherein said flow rate is increased by at least 20%.

24. A process comprising:
   a) preparing caprolactam by Beckmann rearrangement of cyclohexanone oxime in the presence of sulphuric acid to obtain a rearrangement mixture.
   b) neutralizing the rearrangement mixture with ammonia, resulting in phase separation to obtain an aqueous caprolactam mixture
   c) countercurrently extracting the caprolactam from the aqueous caprolactam mixture in an extraction column with the aid of an organic solvent for caprolactam that is not miscible with water to form an organic solvent-caprolactam mixture,
   d) releasing the caprolactam from the organic solvent-caprolactam mixture by means of extraction with water, and
   e) (i) pre-extracting said aqueous caprolactam mixture in a mixer/settler with an organic solvent before step a) and/or (ii) pre-extracting said organic solvent-caprolactam mixture in a mixer/settler with water before step b).

25. A process comprising:
a) preparing caprolactam by Beckmann rearrangement of cyclohexanone oxime in the presence of sulfuric acid to obtain a rearrangement mixture,
b) neutralizing the rearrangement mixture with ammonia, resulting in phase separation to obtain an aqueous caprolactam mixture, and
c) extracting the caprolactam from the aqueous caprolactam mixture with the aid of an organic solvent for caprolactam which is not miscible with water in a countercurrent extraction column, wherein a pre-extraction with an organic solvent immiscible with water in a mixer/settler is conducted prior to said extraction in the extraction column.

26. Process according to claim 24, wherein substantially all of the caprolactam formed in the Beckmann rearrangement in said aqueous caprolactam mixture.

27. Process according to claim 25, wherein substantially all of the caprolactam formed in the Beckmann rearrangement in said aqueous caprolactam mixture.

* * * * *